US012324678B2

(12) United States Patent
Zhao et al.

(10) Patent No.: US 12,324,678 B2
(45) Date of Patent: Jun. 10, 2025

(54) MALE PENIS SITE MAGNETIC RESONANCE IMAGING INTEGRATED COIL HAVING ERECTION ASSISTING FUNCTION

(71) Applicant: The Second Hospital of Tianjin Medical University, Tianjin (CN)

(72) Inventors: Yang Zhao, Tianjin (CN); Dengyi Duan, Tianjin (CN); Jing Peng, Tianjin (CN); Yuanjie Niu, Tianjin (CN)

(73) Assignee: The Second Hospital of Tianjin Medical University, Tianjin (CN)

( * ) Notice: Subject to any disclaimer, the term of this patent is extended or adjusted under 35 U.S.C. 154(b) by 0 days.

(21) Appl. No.: 18/668,828

(22) PCT Filed: Oct. 31, 2022

(86) PCT No.: PCT/CN2022/128708
§ 371 (c)(1),
(2) Date: May 20, 2024

(87) PCT Pub. No.: WO2023/093467
PCT Pub. Date: Jun. 1, 2023

(65) Prior Publication Data
US 2025/0107749 A1 Apr. 3, 2025

(30) Foreign Application Priority Data
Nov. 29, 2021 (CN) .......................... 202111429987.5

(51) Int. Cl.
*A61B 5/00* (2006.01)
*A61B 5/02* (2006.01)
(Continued)

(52) U.S. Cl.
CPC ........ *A61B 5/4393* (2013.01); *A61B 5/02007* (2013.01); *A61B 5/055* (2013.01);
(Continued)

(58) Field of Classification Search
None
See application file for complete search history.

(56) References Cited

U.S. PATENT DOCUMENTS

2015/0305647 A1* 10/2015 Noras .................. A61B 5/4381
600/422
2017/0340266 A1 11/2017 Gardner et al.
(Continued)

FOREIGN PATENT DOCUMENTS

| CN | 1124446 A | 6/1996 |
| CN | 2788741 Y | 6/2006 |

(Continued)

OTHER PUBLICATIONS

Zhi-ming, Li et al., "Application of MRI After Inflatable Penile Prosthesis Implantation for Erectile Dysfunction," 3 Chinese Journal of CT and MRI No. 3 pp. 54-55 (Jul. 2005).

(Continued)

*Primary Examiner* — Jonathan Cwern
(74) *Attorney, Agent, or Firm* — Reising Ethington P.C.

(57) ABSTRACT

A male penis site magnetic resonance imaging integrated coil having an erection assisting function includes a cover body, a negative pressure suction erection assisting apparatus, a programmable erection degree control system, and a multi-channel magnetic resonance imaging coil, and is connected to a full-automatic magnetic resonance contrast agent injection system through a pipeline. The integrated coil is similar to a penis in shape and can be used for penis magnetic resonance imaging to obtain a high-quality image; the negative pressure suction erection assisting apparatus can enable a patient having erectile dysfunction to reach a penile erection state without injection of an erection assisting drug. By adjusting blood flow volume and blood flow speed of a penile blood vessel through the erection degree control system, penis cavernous body angiography can be (Continued)

performed to achieve non-invasive diagnosis of the patient having erectile dysfunction, and cavernosography is expected to be replaced.

9 Claims, 4 Drawing Sheets (51) Int. Cl.
*A61B 5/055* (2006.01)
*G01R 33/34* (2006.01)
*G01R 33/563* (2006.01)

(52) U.S. Cl.
CPC ...... *A61B 5/6831* (2013.01); *G01R 33/34046* (2013.01); *G01R 33/34084* (2013.01); *G01R 33/5635* (2013.01)

(56) References Cited

U.S. PATENT DOCUMENTS

| | | | |
|---|---|---|---|
| 2021/0015700 A1 | 1/2021 | Truckai et al. | |
| 2021/0113424 A1 | 4/2021 | Yates | |

FOREIGN PATENT DOCUMENTS

| | | | |
|---|---|---|---|
| CN | 101589985 | A | 12/2009 |
| CN | 201516039 | U | 6/2010 |
| CN | 201676051 | U | 12/2010 |
| CN | 103796619 | A | 5/2014 |
| CN | 104822318 | A | 8/2015 |
| CN | 206700294 | U | 12/2017 |
| CN | 207051471 | U | 2/2018 |
| CN | 209172306 | U | 7/2019 |
| CN | 212756840 | U | 3/2021 |
| CN | 114176879 | A | 3/2022 |
| KR | 20090024899 | A | 3/2009 |

OTHER PUBLICATIONS

First Office Action issued in priority Chinese App. No. 202111429987.5 (Aug. 8, 2023).
English translation of first Office Action issued in priority Chinese App. No. 202111429987.5 (Aug. 8, 2023).
Second Office Action issued in priority Chinese App. No. 202111429987.5 Feb. 27, 2024).
English translation of second Office Action issued in priority Chinese App. No. 202111429987.5 (Feb. 27, 2024).
International Search Report issued in corresponding International (PCT) App. No. PCT/CN2022/128708 (Dec. 15, 2022).
English translation of International Search Report issued in corresponding International (PCT) App. No. PCT/CN2022/128708 (Dec. 15, 2022).
Corrected English Translation of first Office Action issued in priority Chinese App. No. 202111429987.5 (Aug. 8, 2023).
Corrected English Translation of second Office Action issued in priority Chinese App. No. 202111429987.5 Feb. 27, 2024).
English (machine) translation of CN 201516039 U.
English (machine) translation of CN 207051471 U.
English (machine) translation of CN 209172306 U.
English (machine) translation of KR 20090024899 A.

* cited by examiner

MALE PENIS SITE MAGNETIC RESONANCE IMAGING INTEGRATED COIL HAVING ERECTION ASSISTING FUNCTION

CROSS-REFERENCE TO RELATED APPLICATION

This patent application is a national stage application of International Patent Application No. PCT/CN2022/128708, filed on Oct. 31, 2022, which claims the benefit and priority of Chinese Patent Application No. 202111429987.5, filed with the China National Intellectual Property Administration on Nov. 29, 2021, the disclosure of which is incorporated by reference herein in its entirety as part of the present application.

TECHNICAL FIELD

The present disclosure relates to a programmed erection and magnetic resonance scanning integrated coil for penile erection, ejaculation function and cavernous arteriovenous network angiography.

BACKGROUND

Penile erectile and ejaculation dysfunction are common andrological diseases. At present, imaging diagnosis for penile erectile dysfunction includes angiography and Doppler ultrasound. However, angiography is an invasive examination and expensive. Although the Doppler ultrasound is a non-invasive examination, its image contrast is poor, and the diagnosis result is closely related to the technical level of an operator and the cooperation degree of a patient.

Magnetic resonance imaging (MRI) has good soft tissue resolution and gradually occupies an important position in penis examination. However, the existing penis magnetic resonance imaging generally adopts a body coil or pelvic coil, which leads to large field of view, affecting the accurate diagnosis of penis site.

Imaging diagnosis for the penile erectile dysfunction generally needs to be performed after penile erection, including the use of vasoactive drugs and continuous infusion of normal saline. However, the above methods have the disadvantages of strong invasiveness and many side effects, and are easy to cause repugnance of the patient. Negative pressure suction technology, which is commonly used to treat penile erectile dysfunction, is also a method for assisting penile erection with good safety and controllability.

SUMMARY

For the disadvantages in the prior art, an objective of the present disclosure is to provide a programmed erection instrument and magnetic resonance scanning integrated coil for penile erection, ejaculation function and cavernous arteriovenous network angiography. The integrated coil is a sleeve device in fit with the shape of penis, which can obtain images with excellent soft tissue resolution in small field of view. The device is equipped with an automatic negative pressure suction apparatus, which can make the penis erect controllably under negative pressure suction and make the penile blood vessels fill and dilatate controllably, so as to achieve noninvasive angiography of the penis, and achieve the purpose of noninvasive diagnosis of ED patients under magnetic resonance. Meanwhile, an ejaculation stimulating system can induce the erectile penis to ejaculate, so as to evaluate the ejaculation function.

In order to solve the technical problem above, a male penis site magnetic resonance imaging integrated coil having an erection assisting function is provided by the present disclosure, including a cover body, and a fixing belt. The cover body includes a sleeve connected to a shield, the sleeve and the shield are in flexible connection, and each of the sleeve and the shield is made of a resin material. A first coil is embedded into a sleeve body, and a second coil is embedded into a shield body. Each of the first coil and the second coil is a multi-channel magnetic resonance imaging coil. The multi-channel magnetic resonance imaging coil is plugged into a coil interface of a magnetic resonance imaging device through an adaptor. The integrated coil further includes a negative pressure suction erection assisting apparatus, and a programmable erection degree control system. The negative pressure suction erection assisting apparatus includes a negative pressure cylinder, and a negative pressure aspirator. The negative pressure cylinder is arranged in a chamber of the sleeve, a negative pressure pipe is connected between the negative pressure cylinder and the negative pressure aspirator, and a pressure gauge is arranged on the negative pressure pipe. An exhaust hole is formed in the negative pressure cylinder, and a first butterfly needle valve is arranged at the exhaust hole. The programmable erection degree control system includes a controller, and the negative pressure aspirator and the pressure gauge are both connected to the controller. The controller is configured to control pressure magnitude in the negative pressure pipe, a pressure change rate, and a pressure duration. A contrast agent injection hole is formed in one side of a front end of the negative pressure cylinder, and the contrast agent injection hole is provided with a second butterfly needle valve, and is connected to a full-automatic magnetic resonance contrast agent injection system by means of a pipeline.

Further, according to the integrated coil of the present disclosure:

A flexible connection structure between the sleeve and the shield is that a through hole is formed in a central part of the shield, and a root of the sleeve is hermetically connected to the through hole of the shield by a latex ring, thus making a connection curvature between the shield and the sleeve adjustable.

The shield is a triangular curved plate, an inner curved surface of the curved plate is in fit with contour of male perineum, the shape of an inner cavity of the negative pressure cylinder is in fit with a contour line of male penis, and an inner side surface of the shield and an inner wall of the negative pressure cylinder are both provided with soft underlayers.

The negative pressure cylinder is in the shape of a cylindrical cup, and is made of a hard material. A tail end of the negative pressure cylinder is provided with an opening which is connected to the negative pressure pipe. A bottom end of the negative pressure cylinder employs an arc edge structure rolling outwards. An inner bottom end of the negative pressure cylinder is provided with an inflatable rubber ring, and the inflatable rubber ring has a manual adjustment mode and an automatic adjustment mode, where the automatic adjustment mode is regulated by the controller.

The controller controls the negative pressure aspirator to suck gas in the negative pressure cylinder to form a negative pressure. The controller maintains a negative pressure state of the negative pressure cylinder by controlling the negative pressure aspirator to continuously provide negative pressure suction. The controller controls a contraction or relaxation state, and tension degree and time of the inflatable rubber ring. The first butterfly needle valve is in manual control, and the second butterfly needle valve is in manual control or controlled by the controller.

The fixing belt includes a waistband connected to left and right sides of the shield, and a traction belt connected to a bottom end of the protective cover. Ends of the waistband and the traction belt are connected together by an adjustable slip-on buckle structure.

An outer surface of the sleeve is provided with a trend groove of the negative pressure pipe.

The multi-channel magnetic resonance imaging coil may be a receiving coil with four channels, eight channels, sixteen channels, thirty-two channels, or more channels. The multi-channel magnetic resonance imaging coil includes multiple groups of coil units, and a coil assembly, which is divided into a first coil and a second coil. Various coil units of the first coil are combined to form a sleeve structure, which can wrap around a penis site to perform magnetic resonance imaging on the penis, so as to obtain a thin-layer, high-matrix and small-field image. Various coil units of the second coil are combined to form a curved triangular structure, which can be closely attached to a perineum site to perform magnetic resonance imaging on vascular plexus at the root of the penis and the perineum site.

The integrated coil is further provided with an ejaculation stimulating device.

Compared with the prior art, the present disclosure has the following beneficial effects:

According to the advantages of the programmed erection instrument and magnetic resonance scanning integrated coil for penile erection, ejaculation function and cavernous arteriovenous network angiography provided by the present disclosure, a coil device suitable for penis specific imaging of a patient with erectile dysfunction is provided, which not only can obtain ultra-high soft tissue resolution images, but also can make the penis erect through a negative pressure suction device without injecting drugs, thus achieving better imaging effect. Meanwhile, through the controllable adjustment of negative pressure suction, penile blood vessels can be controllably dilated, and the blood flow speed of the penile blood vessels can be controlled, thus achieving non-invasive angiography without injecting a contrast agent. Through the pumping and deflation of the negative pressure cylinder by the control system, the penile blood vessels of the patient with ED are controllably dilated and contracted, so as to achieve the purpose of diagnosis and functional evaluation of the patient with ED. Injection of the contrast agent through the contrast agent injection hole and a full-automatic magnetic resonance contrast agent injection system can further optimize cavernous arteriovenous network angiography

BRIEF DESCRIPTION OF THE DRAWINGS

FIG. 3A is a schematic diagram of a first coil, and FIG. 3B is a schematic diagram of a second coil.

In the drawings: 1—sleeve, 2—negative pressure cylinder; 3—negative pressure pipe; 4—pressure gauge; 5—negative pressure aspirator; 6—first coil; 7—second coil; 8—contrast agent injection hole; 9—exhaust hole; 10—shield; 11—waistband; 12—controller; 13—adaptor; 14—snap-on buckle structure; 15—latex ring; 16—inflatable rubber ring; 101—coil unit.

DETAILED DESCRIPTION OF THE EMBODIMENTS

The following clearly and completely describes the technical solutions in the embodiments of the present disclosure with reference to the accompanying drawings in the embodiments of the present disclosure. Apparently, the described embodiments are merely a part rather than all of the embodiments of the present disclosure. All other embodiments obtained by a person of ordinary skill in the art based on the embodiments of the present disclosure without creative efforts shall fall within the scope of protection of the present disclosure.

Figure 1:
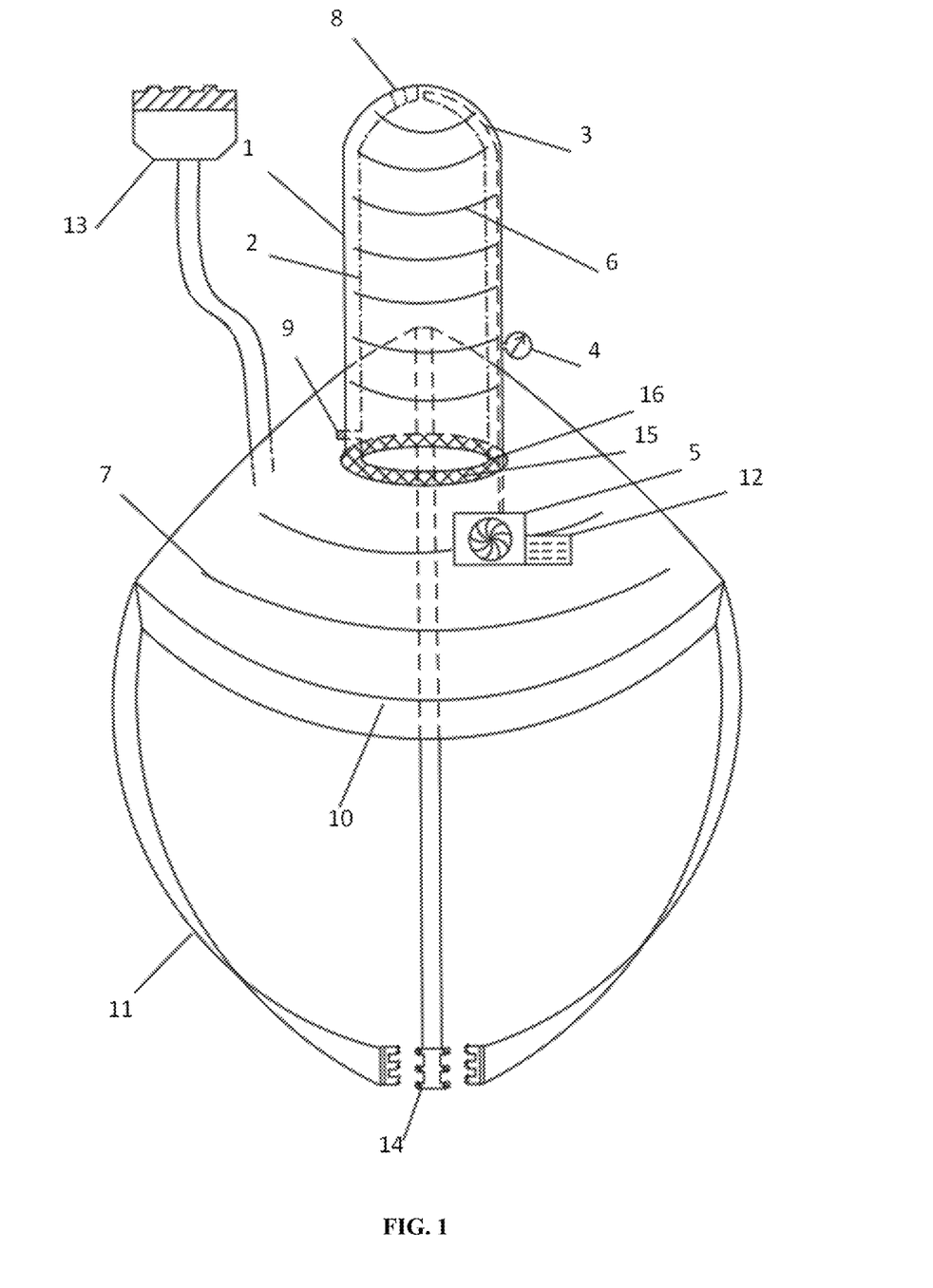
FIG. 1 is a front view of an integrated coil according to the present disclosure.
Figure 2:
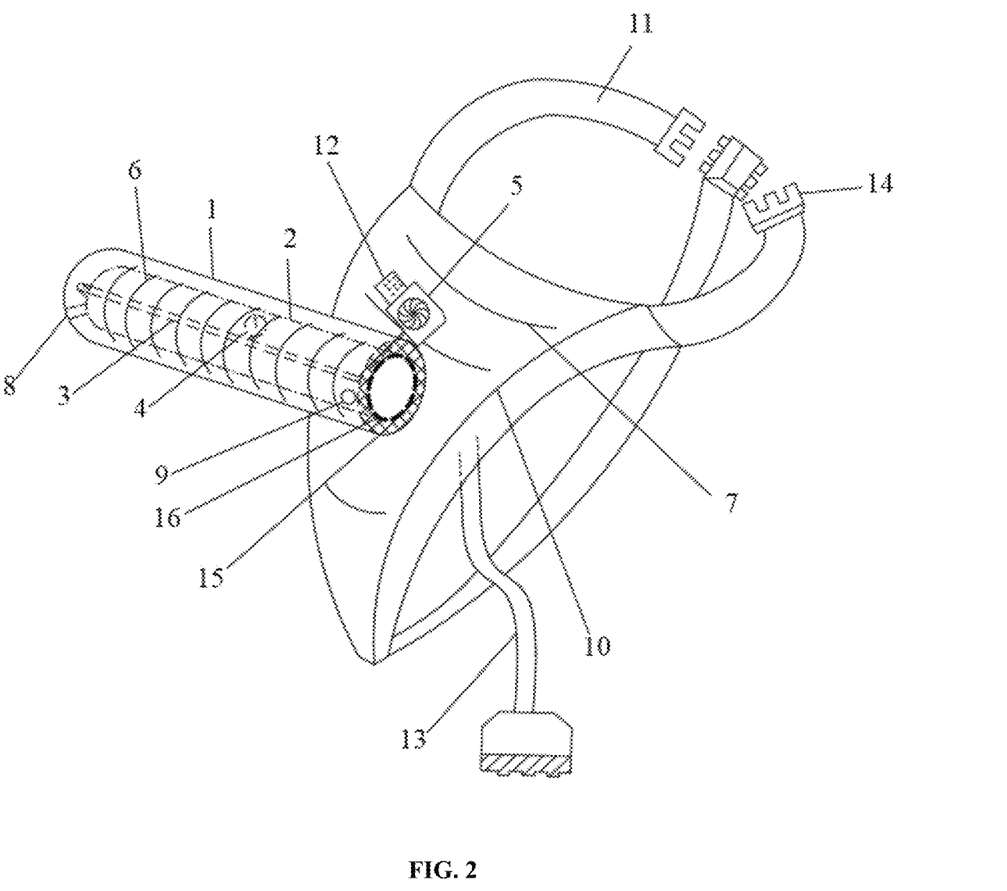
FIG. 2 is a schematic diagram of a three-dimensional structure of an integrated coil according to the present disclosure.
Figure 3A:
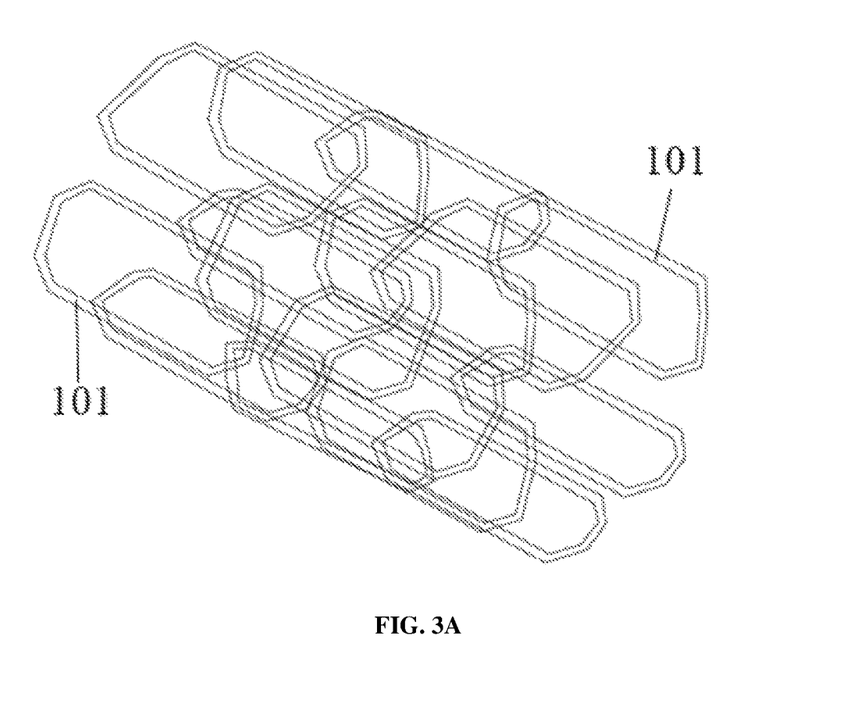
FIGS. 3A-3B are schematic diagrams of the combination of coil units of a first coil and a second coil according to the present disclosure.
Figure 3B:
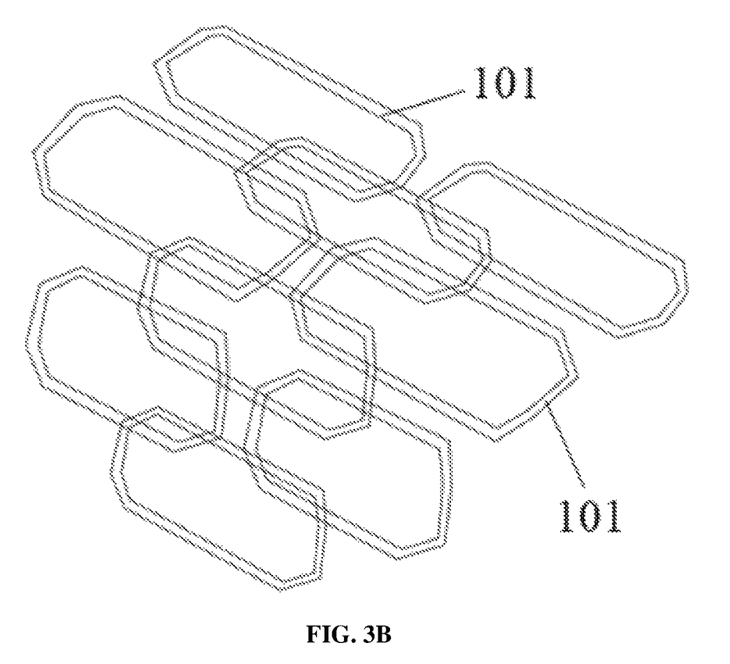

As shown in FIG. 1 and FIG. 2, a male penis site magnetic resonance imaging integrated coil having an erection assisting function includes a cover body, and a fixing belt. The cover body includes a sleeve 1 connected to a shield 10, the sleeve 1 is in flexible connection with the shield 10, and the sleeve 1 and the shield 10 are both made of resin materials. The shield 10 is a triangular curved plate, an inner curved surface of the curved plate is in fit with the contour of male perineum, and an inner side surface of the shield 10 is provided with a soft underlayer which can wrap around the perineum site. A flexible connection structure between the sleeve 1 and the shield 10 is that a through hole is formed in a central part of the shield 10, and a root of the sleeve 1 is hermetically connected to the through hole of the shield 10 by a latex ring 15, thus making a connection curvature between the shield 10 and the sleeve 1 adjustable. The fixing belt includes waistbands 11 connected to left and right sides of the shield 10, and a traction belt connected to a bottom end of the protective cover 10. Ends of the waistbands and the traction belt are connected together by an adjustable slip-on buckle structure 14. When the coil is worn and fixed, the waistbands at both ends can wrap around the waist and buttocks of a patient in an arc, and the length can be freely adjusted through the slip-on buckle structure, which is suitable for patients with different body types. A first coil 6 is embedded into a sleeve 1 body, and a second coil 7 is embedded into a shield 10 body. The first coil 6 and the second coil 7 are both multi-channel magnetic resonance imaging coils. The multi-channel magnetic resonance imaging coil is a receiving coil with four channels, eight channels, sixteen channels, thirty-two channels, or more channels. The multi-channel magnetic resonance imaging coil includes multiple groups of coil units 101, and a coil assembly. The coil units 101 are combined in a partially staggered and overlapping coupling mode. As shown in FIG. 3A, the coil units 101 of the first coil 6 are combined to form a sleeve structure, which can closely wrap around a penis site to perform magnetic resonance imaging on the penis, so as to obtain a thin-layer, high-matrix and small-field image. As shown in FIG. 3B, the coil units 101 of the second coil 7 are combined to form a curved triangular structure, which can be closely attached to the perineum site to perform magnetic resonance imaging on vascular plexus at the root of the penis and the perineum site. It should be noted that the number of the coil units 101 should not be limited to the number shown in FIG. 3A and FIG. 3B, which may be set as other number. The multi-channel magnetic resonance imaging coil is plugged into a signal receiving terminal of a magnetic resonance imaging device through an adaptor 13.

The integrated coil further includes a negative pressure suction erection assisting apparatus, and a programmable erection degree control system. The negative pressure suction erection assisting apparatus includes a negative pressure cylinder 2, and a negative pressure aspirator 5. The negative pressure 2 is arranged in a chamber of the sleeve 1, that is, the first coil 6 is encapsulated in the sleeve 1 body. The sleeve 1 is internally coated with the negative pressure cylinder 2, the negative pressure cylinder 2 is in the shape of a cylindrical cup, and is made of a hard material. The shape of an inner cavity of the negative pressure cylinder 2 is in fit with a contour line of the male penis, such that the second coil 7 inside the sleeve 1 body can wrap around and is in fit with the erectile penis. A negative pressure pipe 3 is connected between the negative pressure cylinder 2 and the negative pressure aspirator 5, that is, a tail end (front end) of the negative pressure cylinder 2 is provided with an opening which is connected to the negative pressure pipe 3. A bottom end of the negative pressure cylinder 2 is of an arc edge structure rolling outwards, which can be closely attached to the skin of the perineum. An inner wall of the negative pressure cylinder 2 is provided with a soft underlayer. A bottom end of the negative pressure cylinder 2 is provided with an inflatable rubber ring 16, which can be in fit with the root of the penis to guarantee the pressure of the negative pressure cylinder 2, thus maintaining an erection state of the penis. The inflatable rubber ring 16 has a manual adjustment mode and an automatic adjustment mode. The tightness of the inflatable rubber ring 16 can be manually adjusted or adjusted by the controller 12. An outer surface of the sleeve 1 is provided with a trend groove for the negative pressure pipe 3, which is used for fixing the negative pressure pipe 3. The negative pressure pipe 3 is provided with a pressure gauge 4. An exhaust hole 9 is formed in the negative pressure cylinder 2, and a first butterfly needle valve is arranged at the exhaust hole 9. The first butterfly needle valve is in manual control, and the exhaust of the negative pressure cylinder 2 can be manually controlled in case of emergency.

The programmable erection degree control system includes a controller 12, and a remote-control device. The negative pressure aspirator 5 and the pressure gauge 4 are both connected to the controller 12. The magnitude and rate of the suction pressure of the negative pressure aspirator 5 are adjustable, and the passing gas flow can be monitored. The negative pressure aspirator 5 is fixed to the shield 10 in a detachable manner. The controller 12 is used for controlling pressure magnitude in the negative pressure cylinder 2, a pressure change rate, and the pressure duration.

In the present disclosure, a contrast agent injection hole 8 is formed in one side of a front end of the negative pressure cylinder 2, and the contrast agent injection hole 8 is provided with a second butterfly needle valve and is connected to a full-automatic magnetic resonance contrast agent injection system by means of a pipeline. The second butterfly needle valve is in manual control or controlled by the controller, and whether or not to inject contrast agent into the negative pressure cylinder 2 and the amount of contrast agent injected into the negative pressure cylinder 2 in the sleeve 1 through a connecting pipeline are controlled through the on-off state and opening-closing degree of the butterfly needle valve.

In the present disclosure, the programmable erection degree control system may achieve negative pressure formation, negative pressure maintenance, and pressure control. The achievement of negative pressure formation is to form a negative pressure by sucking the gas in the negative pressure cylinder 2 through the negative pressure aspirator 5. There are two situations to achieve negative pressure maintenance: the first is that the negative pressure aspirator 5 continues to provide negative pressure suction to maintain a negative pressure state of the negative pressure cylinder 2; and the second is that the contraction and relaxation degree and time of the inflatable rubber ring 16 are manually or automatically controlled to control the opening and closing of blood vessels at the root of penis to maintain the erection of penis. The achievement of pressure control is that an automatic negative pressure suction mode and a manual model are merged, and a remote-control operation is provided, so as to control the erection degree by means of the control of gas pressure and the tension control of rubber ring. The control of gas pressure is to control the opening degree of the blood vessels at the root of penis by controlling the magnitude and rate of the negative pressure suction pressure, and the tension control of inflatable rubber ring 16 is to control the opening degree of the blood vessels at the root of penis by controlling the tightness of the rubber ring by controller, and to control the erection degree of penis by controlling the blood flow volume and blood flow speed of penile blood vessels.

The integrated coil may be further provided with an ejaculation stimulating device to stimulate the erectile penis, induce ejaculation, and evaluate an ejaculation threshold of the patient, so as to evaluate the ejaculation function of the patient.

Embodiment

The integrate loop provided by the present disclosure is sleeved on the penis of a patient with erectile dysfunction, and the slip-on buckle structure of the waistband is adjusted, the bottom of the negative pressure cylinder 2 is close to the perineal skin of a wearer by means of an arc design of the bottom end of the negative pressure cylinder 2, and the shield 10 is stably fixed to the perineum, thereby ensuring that the internal pressure change of the negative pressure cylinder 2 will not lead to gas leakage in the erection assisting and imaging process. The controller 12 is configured to set an appropriate negative pressure suction pressure and rate for the negative pressure aspirator 5, such that the penile blood vessels can be controllably dilated under the negative pressure suction, the blood flow volume of the penis is increased, and the penis reaches an erection state. The inflatable rubber ring 16 is adjusted to maintain the erection state of the penis for magnetic resonance imaging, so as to obtain a high-resolution magnetic resonance image. In this embodiment, by setting different programmed negative pressure suction pressures and rates by the controller 12, the blood flow speed of penile blood vessels can be adjusted, so as to achieve non-invasive cavernous arteriovenous network angiography under magnetic resonance imaging of the penis site, evaluate the stenosis degree and occlusion function of cavernous arteriovenous network, and clarify the etiology of the patient with erectile dysfunction. When the non-invasive angiography under magnetic resonance imaging is poor, the magnetic resonance contrast agent can be injected into the corpus cavernosum via a connecting pipe through a full-automatic magnetic resonance contrast agent injection system for further development and angiography of the penile blood vessels. In the process of examination, when the patient feels uncomfortable, the exhaust hole 9 can be opened to rapidly eliminate the negative pressure state of the negative pressure cylinder 2, so as to provide safe and reliable guarantee measures for the patient. During the examination, the erectile penis is induced to ejaculate by rectal electrical stimulation through a selected penis ejaculation stimulating device as needed, and a semen flow direction is dynamically observed under magnetic resonance imaging, so as to clarify the etiology of ejaculation dysfunction. Meanwhile, the ejaculation threshold of patient is evaluated through different stimulation intensities, and the ejaculation function of the patient can be evaluated in combination with brain functional imaging.

To sum up, the integrated coil provided by the present disclosure is not only in fit with the penis in shape, but also can be specially used for penis magnetic resonance imaging to obtain thin-layer, high-matrix and small-field images. Moreover, the negative pressure suction erection assisting apparatus can enable a patient having erectile dysfunction to reach a penile erection state without injection of an erection assisting drug, and the quality of the MRI (magnetic resonance imaging) image is improved. The blood flow volume and blood flow speed of the penile blood vessel are adjusted by means of the negative pressure control system, penis cavernous body angiography can be performed, non-invasive diagnosis and erectile function evaluation of the patient with erectile dysfunction can be achieved under magnetic resonance imaging, and cavernosography is expected to be replaced. Moreover, the full-automatic contrast agent injection system can further optimize the arteriovenous network angiography of penis cavernous body by injecting the contrast agent under the condition of poor noninvasive angiography. By stimulating the erectile penis to ejaculate, the ejaculation function of the patient can be evaluated, so as to provide more comprehensive diagnosis and treatment value for the patients.

It should be noted that it is apparent to those skilled in the art that the present disclosure is not limited to the details of the above exemplary embodiments and can be realized in other specific forms without departing from the spirit or basic characteristics of the present disclosure. Therefore, the embodiments should be considered in all respects as exemplary and non-limiting. Under the inspiration of the present disclosure, those of ordinary skill in the art can make many deformations without departing from the intention of the present disclosure, which are all within the protection of the present disclosure.

What is claimed is:

1. A male penis site magnetic resonance imaging integrated coil having an erection assisting function, comprising a cover body, and a fixing belt, wherein the cover body comprises a sleeve (1) connected to a shield (10), the sleeve (1) and the shield (10) are in flexible connection, and each of the sleeve (1) and the shield (10) is made of a resin material; a first coil (6) is embedded into a sleeve (1) body, and a second coil (7) is embedded into a shield (10) body; each of the first coil (6) and the second coil (7) is a multi-channel magnetic resonance imaging coil; the multi-channel magnetic resonance imaging coil is plugged into a coil interface of a magnetic resonance imaging device through an adaptor; the first coil (6) comprises various coil units (101) configured as a sleeve structure, which is able to wrap around a penis site and the second coil (7) comprises various coil units (101) configured as a curved triangular structure, which is able to be closely attached to a perineum site;

the integrated coil further comprises a negative pressure suction erection assisting apparatus, and a programmable erection degree control system; the negative pressure suction erection assisting apparatus comprises a negative pressure cylinder (2), and a negative pressure aspirator (5); the negative pressure cylinder (2) is arranged in a chamber of the sleeve (1), a negative pressure pipe (3) is connected between the negative pressure cylinder (2) and the negative pressure aspirator (5), and a pressure gauge (4) is arranged on the negative pressure pipe (3); the negative pressure cylinder (2) is provided with an exhaust hole (9), and a first butterfly needle valve is arranged at the exhaust hole (9); the programmable erection degree control system comprises a controller (12), and the negative pressure aspirator (5) and the pressure gauge (4) are both connected to the controller (12); and the controller (12) is configured to control pressure magnitude in the negative pressure cylinder (2), a pressure change rate and a pressure duration; the controller (12) is configured to set programmed negative pressure suction pressures with different magnitudes and rates, so as to adjust blood flow velocity of a penile blood vessel to achieve non-invasive cavernous arteriovenous network angiography under magnetic resonance imaging of the penis site, thus evaluating the degree of stenosis and occlusion function of cavernous arteriovenous network;

the shield (10) is a triangular curved plate, an inner curved surface of the curved plate is in fit with contour of male perineum, the shape of an inner cavity of the negative pressure cylinder (2) is in fit with a contour line of male penis, and an inner side surface of the shield (10) and an inner wall of the negative pressure cylinder (2) are both provided with soft underlayers; a bottom end of the negative pressure cylinder (2) is designed as an arc;

one side of a front end of the negative pressure cylinder (2) is provided with a contrast agent injection hole (8), and the contrast agent injection hole (8) is provided with a second butterfly needle valve, and is connected to a full-automatic magnetic resonance contrast agent injection system by means of a pipeline; and the full-automatic magnetic resonance contrast agent injection system is configured to inject a magnetic resonance contrast agent into corpus cavernosum via a connecting pipe when non-invasive angiography under the magnetic resonance imaging is poor for further development and angiography of the penile blood vessel.

2. The integrated coil according to claim 1, wherein a central part of the shield (10) is provided with a through hole, and a root of the sleeve (1) is hermetically connected to the through hole of the shield (10) by a latex ring (15), thus making a connection curvature between the shield (10) and the sleeve (1) adjustable.

3. The integrated coil according to claim 2, wherein the negative pressure cylinder (2) is in the shape of a cylindrical cup, and is made of a hard material; a tail end of the negative pressure cylinder (2) is provided with an opening which is connected to the negative pressure pipe (3); a bottom end of the negative pressure cylinder (2) employs an arc edge structure rolling outwards; an inner bottom end of the negative pressure cylinder (2) is provided with an inflatable rubber ring (16), and the inflatable rubber ring (16) has a manual adjustment mode and an automatic adjustment mode, where the automatic adjustment mode is regulated by the controller (12).

4. The integrated coil according to claim 3, wherein the controller (12) controls the negative pressure aspirator (5) to suck gas in the negative pressure cylinder (2) to form a negative pressure; the controller (12) maintains a negative pressure state of the negative pressure cylinder (2) by controlling the negative pressure aspirator (5) to continuously provide negative pressure suction; and the controller (12) controls a contraction or relaxation state, and tension degree and time of the inflatable rubber ring (16), and comprises a negative pressure forming system, a negative pressure maintaining system, and a pressure control system.

5. The integrated coil according to claim 1, wherein the first butterfly needle valve is configured to be controlled manually, and the second butterfly needle valve is configured to be controlled manually or controlled by the controller.

6. The integrated coil according to claim 1, wherein the fixing belt comprises waistbands (11) connected to left and right sides of the shield (10), and a traction belt connected to a bottom end of the protective cover (10), wherein ends of the waistbands and the traction belt are connected together by an adjustable slip-on buckle structure (14).

7. The integrated coil according to claim 1, wherein an outer surface of the sleeve (1) is provided with a trend groove of the negative pressure pipe (3).

8. The integrated coil according to claim 1, wherein the multi-channel magnetic resonance imaging coil is a receiving coil with four channels, eight channels, sixteen channels, or thirty-two channels; the multi-channel magnetic resonance imaging coil comprises a plurality of groups of coil units (101), and a coil assembly.

9. The integrated coil according to claim 1, wherein the integrated coil is further provided with an ejaculation stimulating device.

\* \* \* \* \*